(12) United States Patent
Kitamura et al.

(10) Patent No.: US 9,217,716 B2
(45) Date of Patent: Dec. 22, 2015

(54) METHOD FOR TESTING CHARGE GENERATION LAYER AND PROCESS FOR MANUFACTURING ELECTROPHOTOGRAPHIC PHOTORECEPTORS ON LARGE SCALE

(71) Applicant: CANON KABUSHIKI KAISHA, Tokyo (JP)

(72) Inventors: Wataru Kitamura, Matsudo (JP); Ryoichi Tokimitsu, Kashiwa (JP); Masaki Nonaka, Toride (JP); Mai Murakami, Kashiwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 81 days.

(21) Appl. No.: 14/229,525

(22) Filed: Mar. 28, 2014

(65) Prior Publication Data

US 2014/0295058 A1 Oct. 2, 2014

(30) Foreign Application Priority Data

Apr. 1, 2013 (JP) .................................. 2013-076503

(51) Int. Cl.
*G01N 21/95* (2006.01)
*G03G 5/05* (2006.01)
*G03G 5/06* (2006.01)
*G03G 5/10* (2006.01)
*G03G 5/14* (2006.01)

(52) U.S. Cl.
CPC .............. *G01N 21/95* (2013.01); *G03G 5/0525* (2013.01); *G03G 5/0696* (2013.01); *G03G 5/102* (2013.01); *G03G 5/144* (2013.01)

(58) Field of Classification Search
CPC ....................................................... G01N 21/95
See application file for complete search history.

(56) References Cited

U.S. PATENT DOCUMENTS 6,197,463 B1 * 3/2001 Cais et al. .................. 430/58.05
2007/0003851 A1 * 1/2007 Kawahara et al. ........... 430/59.2

FOREIGN PATENT DOCUMENTS

JP   2003-075362 A    3/2003
JP   2003075362    *   3/2003

* cited by examiner

*Primary Examiner* — Nathan T Leong
(74) *Attorney, Agent, or Firm* — Canon USA, Inc., IP Division

(57) ABSTRACT

A method is provided for testing a charge generation layer disposed directly on an undercoat layer disposed directly on an aluminum-based cylindrical support member formed by extrusion and drawing having a periphery not subjected to cutting work. The method includes testing the charge generation layer for a defect or a suspected defect by irradiating the charge generation layer with light, and receiving reflected light from the charge generation layer with a light receiving device. The light emitted to the charge generation layer has a wavelength within the range of the absorption wavelengths of the charge generation layer, and whose transmittance to the undercoat layer is 0.3% or less.

10 Claims, 1 Drawing Sheet

METHOD FOR TESTING CHARGE
GENERATION LAYER AND PROCESS FOR
MANUFACTURING
ELECTROPHOTOGRAPHIC
PHOTORECEPTORS ON LARGE SCALE

BACKGROUND

1. Field of Art

The present disclosure relates to a method for testing a charge generation layer and to a process for manufacturing electrophotographic photoreceptors on a large scale.

2. Description of the Related Art

An electrophotographic photoreceptor of an electrophotographic apparatus includes a support member, an undercoat layer on the surface of the support member, and a charge generation layer containing an organic charge generation material and a charge transport layer containing a charge transport material, disposed on the undercoat layer.

The electrophotographic photoreceptor is manufactured by applying a charge generation coating liquid in which a charge generation material and a binding resin are dissolved or dispersed in a medium onto the surface of the support member to form a coating film, and drying the coating film.

The coating liquid is evenly applied to a uniform thickness so that the electrophotographic photoreceptor can form images having no unevenness. However, stagnation of and finger touch on the coating liquid during coating operation can cause unevenness in the thickness of the coating film. Also, evaporation of the solvent may adversely affect the evenness in thickness. Since large unevenness in the thickness of the coating film can result in image defects, coating films must be screened for uneven thickness in a testing step in the manufacturing process of electrophotographic photoreceptors. In particular, unevenness of the charge generation layer in thickness (hereinafter may be referred to as the defect of the charge generation layer) considerably affects the sensitivity of the electrophotographic photoreceptor, and accordingly tends to cause image defects.

For testing the charge generation layer for unevenness in thickness, the electrophotographic photoreceptor may be visually observed, or subjected to the test of irradiating the electrophotographic photoreceptor with light and receiving the reflected light with a light-receiving device. Japanese Patent Laid-Open No. 2003-75362 discloses a test method for testing electrophotographic photoreceptors for interference fringes and appearance defects at one time. In this method, electrophotographic photoreceptors are irradiated with light having a single wavelength, and a line sensor camera receives the light regularly reflected from the electrophotographic photoreceptor and detects unevenness in the thickness of the charge generation layer by image processing.

The applicant has found that when an undercoat layer having a transmittance of 1% or more for light having a wavelength in the visible region is formed directly on an aluminum cylindrical support member formed by extrusion and drawing and having a periphery not subjected to cutting work, the undercoat layer may not be able to cover the unevenness of the support member.

The unevenness of the aluminum cylindrical support member formed by extrusion and drawing whose periphery has not be subjected to cutting work is in the form of streaks extending in the generating line direction of the support member. Unlike the unevenness in the thickness of the charge generation layer considerably affecting sensitivity, the unevenness of the support member does not easily result in image defects. Even if some unevenness is detected in the support member in a test, such unevenness should be judged to be not defective as long as unevenness in the thickness of the charge generation layer is not detected.

However, if unevenness is detected in a test of the charge generation layer for unevenness in thickness after the charge generation layer has been formed on the undercoat layer on the support member, it cannot be determined whether the detected unevenness results from an uneven thickness of the charge generation layer, which may cause an image defect, or the uneven support member.

SUMMARY

Accordingly, an aspect of the present invention provides a method for testing a charge generation layer performed after the charge generation layer has been formed directly on an undercoat layer that is disposed directly on an aluminum cylindrical support member formed by extrusion and drawing, has a periphery not subjected to cutting work and has an transmittance of 1% or more for light having a wavelength in the visible region, in which it can be determined whether a detected unevenness results from an even thickness of the charge generation layer or the uneven support member. An aspect of the present invention also provides a process for manufacturing electrophotographic photoreceptors on a large scale, including the method for testing the charge generation layer.

According to an aspect of the present invention, a method for testing a charge generation layer of an object including an aluminum-based cylindrical support member formed by extrusion and drawing having a periphery not subjected to cutting work, an undercoat layer disposed directly on the periphery of the support member and having a transmittance of 1% or more for light having a wavelength in the visible region, and the charge generation layer disposed directly on the undercoat layer and having absorption wavelengths. The method includes testing the charge generation layer for a defect or a suspected defect by:

irradiating the charge generation layer with light, and receiving reflected light from the charge generation layer with a light receiving device, wherein the light has a wavelength within the range of the absorption wavelengths of the charge generation layer, and transmittance to the undercoat layer of the light is 0.3% or less.

An aspect of the present invention also provides a process for manufacturing a plurality of electrophotographic photoreceptors on a large scale. The process includes producing objects to be tested, each including an aluminum-based cylindrical support member formed by extrusion and drawing having a periphery not subjected to cutting work, an undercoat layer disposed directly on the periphery of the support member and having a transmittance of 1% or more for light having a wavelength in the visible region, and a charge generation layer disposed directly on the undercoat layer and having absorption wavelengths. The process also includes testing each charge generation layer for a defect or a suspected defect by irradiating the charge generation layer with light, receiving reflected light from the charge generation layer with a light-receiving device, and grouping the objects into the following three groups:

(a) objects having a defect in the charge generation layer;

(b) objects having a suspected defect in the charge generation layer; and (c) objects having no defect or suspected defect in the charge generation layer.

The objects applicable to either the following (i) or (ii) are heat-treated:

(i) objects grouped into (b), but judged in a subsequent visual inspection that the suspected defect is not a defect in the charge generation layer; and (ii) objects grouped into (c), wherein the light has a wavelength within the range of the absorption wavelengths of the charge generation layer, and transmittance to the undercoat layer of the light is 0.3% or less.

In an embodiment of the invention, evenness in the thickness of the charge generation layer can be separated from unevenness of the aluminum-based support member formed by extrusion and drawing having a periphery not subjected to cutting work. Also, in the process of an embodiment of the invention including the test method, electrophotographic photoreceptors can be manufactured on a large scale.

Further features of the present invention will become apparent from the following description of exemplary embodiments with reference to the attached drawings.

DESCRIPTION OF THE EMBODIMENTS

The test method of an embodiment of the present invention tests a charge generation layer of an object including an aluminum cylindrical support member formed by extrusion and drawing having a periphery not subjected to cutting work, an undercoat layer disposed directly on the periphery of the support member, and the charge generation layer disposed directly on the undercoat layer.

The undercoat layer of the object to be tested in the test method of the present embodiment has a transmittance of 1% or more for light having a wavelength in the visible region. The test method includes testing the charge generation layer for a defect and a suspected defect by irradiating the charge generation layer with light and receiving reflected right form the charge generation layer with a light-receiving device. In this testing step, the light with which the charge generation layer is irradiated has a wavelength within the range of the absorption wavelengths of the charge generation layer, and whose transmittance to the undercoat layer is 0.3% or less.

The visible region mentioned herein refers to a range of wavelengths of 380 nm to 780 nm.

For testing the charge generation layer, a light source is used which emits light whose transmittance to the undercoat layer is 0.3% or less. Therefore the light is unlikely to reach the aluminum-based cylindrical support member formed by extrusion and drawing having a periphery not subjected to cutting work, and accordingly, irregular reflection from the support member is reduced. Thus, unevenness of the support member is not defected, and only the unevenness in the thickness of the charge generation layer is detected. If the light transmittance to the undercoat layer is more than 0.3%, unevenness of the support member is easily detected. This makes it difficult to determine whether or not detected unevenness results from an uneven thickness of the charge generation layer (defect of the charge generation layer).

Also, the light used in the testing step has a wavelength in the range of the absorption wavelengths of the charge generation layer. If the wavelength of the light is outside the range of the absorption wavelengths of the charge generation layer, the intensity of reflected light from the charge generation layer does not vary depending on the unevenness in the thickness of the charge generation layer. Accordingly, it becomes difficult to detect unevenness in the thickness of the charge generation layer.

Figure 1:
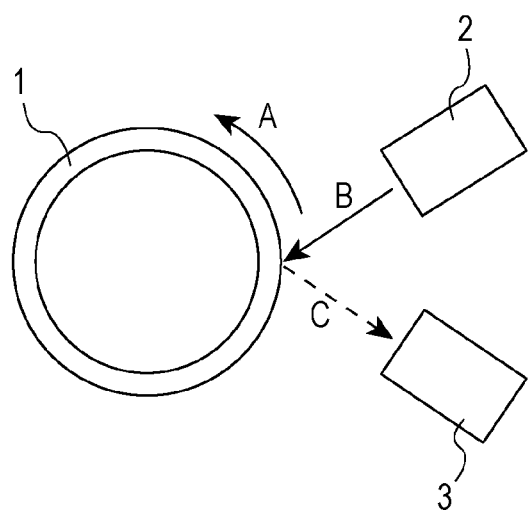
FIG. 1 is a schematic representation of a test method of a charge generation layer according to an embodiment of the present invention.

The testing step will now be described in detail. FIG. 1 is a schematic representation of the support member to be tested in the testing step of the test method of the present embodiment, and a light source and a light-receiving device used in the testing step.

The support member 1 shown in FIG. 1 is an aluminum-based cylindrical support member formed by extrusion and drawing, and whose periphery is not subjected to cutting work. The support member is provided with an undercoat layer (not shown) having a transmittance of 1% or more for light having a wavelength in the visible region directly thereon, and a charge generation layer (not shown) is disposed directly on the undercoat layer. An object to be tested may have this structure.

While the support member 1 is rotated in the direction indicated by arrow A, light is emitted to the support member 1 in the direction indicated by arrow B from the light source 2. The emitted light has a wavelength within the range of the absorption wavelengths of the charge generation layer, and whose transmittance to the undercoat layer is 0.3% or less.

The emitted light is reflected in the direction indicated by arrow C and received with a light-receiving device 3. When a charge generation layer has an uneven thickness, the intensity of the reflected light varies depending on the presence or absence of unevenness in thickness. Therefore, whether or not the charge generation layer has an uneven thickness is determined by analyzing the difference in the intensity of the reflected light.

In the analysis of the difference in the intensity of reflected light, support members judged to be defective (in terms of unevenness in the thickness of the charge generation layer) are not sent to the subsequent step (third step). On the other hand, support members judged to be not defective because there are no defects or suspected defects (described later) are sent to the subsequent step (third step). In the testing step where the difference in the intensity of reflected light is analyzed, some of the detected defects are, however, difficult to correctly judge to be defective or not. These are judged to be suspected defects. The support members whose test results show that the charge generation layer has a suspected defect are then carefully subjected to visual observation test or the like for unevenness in thickness. It is thus determined whether or not the suspected defect is the defect in the thickness of the charge generation layer. Then, the support members whose visual observation results show that the charge generation layer does not have a defect are sent to the subsequent step (third step).

The testing step of the present embodiment is performed after the charge generation layer has been formed, but is not necessarily performed immediately after the formation of the charge generation layer. For example, the testing step may be performed after a charge transport layer has been formed on the charge generation layer, or after a protective layer has been formed on the charge transport layer.

If the testing step is performed after a charge transport layer or a protective layer has been formed on the charge generation layer, a constituent of the charge transport layer or the protective layer may absorb or scatter the light used in the testing step and thus make it difficult to detect the unevenness in the thickness of the charge generation layer. In this case, the amount of light is adjusted so that an amount of light sufficient for the test can reach the charge generation layer. If the charge transport layer or the protective layer absorbs or scatters such a large amount of light that light cannot sufficiently reach the charge generation layer, it is desirable to perform the testing step before forming the charge transport layer or the protective layer.

When the testing step is performed, a photo memory may occur at the charge generation layer depending on the wavelength of the light used for the test. In particular, light having a wavelength of 500 nm or less is liable to cause a photo memory. If the light used for the test has such a wavelength, it is desirable to apply heat treatment to the support members after the testing step. The heat treatment conditions are set according to the degree of the photo memory. In general, the heat treatment is performed at a temperature of 100° C. or more for 10 minutes or more.

Figure 2:
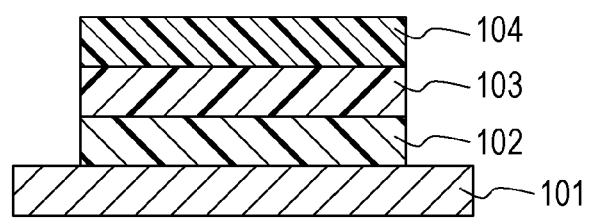
FIG. 2 is a schematic representation of the multilayer structure of an electrophotographic photoreceptor according to an embodiment of the present invention.

The electrophotographic photoreceptor of an embodiment of the present invention includes a support member 101, an undercoat layer 102 disposed on the support member 101, a charge generation layer 103 disposed on the undercoat layer 102, and a charge transport layer 104 disposed on the charge generation layer 103, as shown in, for example, FIG. 2. A protective layer may be further provided on the charge transport layer.

Support Member

The support member is an aluminum-based cylindrical member formed by extrusion and drawing, whose periphery is not subjected to cutting work. The material of the support member may be aluminum or an aluminum alloy. The term "aluminum-based" mentioned herein means that the support member is made of aluminum or an aluminum alloy.

Undercoat Layer

The support member is provided with an undercoat layer thereon. The undercoat layer has a transmittance of 1% or more for light having a wavelength in the visible region.

The undercoat layer can be formed by applying an undercoating liquid prepared by dispersing metal oxide particles and a binding resin in a solvent to form a coating film and drying the coating film. The dispersion is performed using, for example, a homogenizer, an ultrasonic disperser, a ball mill, a sand mill, a roll mill, a vibration mill, an attritor, or a high-speed liquid collision disperser.

Examples of the resin used in the undercoat layer include acrylic resin, allyl resin, alkyd resin, ethyl cellulose resin, ethylene-acrylic acid copolymer, epoxy resin, casein resin, silicone resin, gelatin resin, phenol resin, butyral resin, polyacrylate, polyacetal, polyamide-imide, polyamide, polyallyl ether, polyimide, polyurethane, polyester, polyethylene, polycarbonate, polystyrene, polysulfone, polyvinyl alcohol, polybutadiene, and polypropylene. These resins may be used singly or in combination. Among these resins, polyurethane may be suitably used.

Examples of the metal oxide particles used in the undercoat layer contain particles of at least one metal oxide selected from the group consisting of zinc oxide, titanium oxide, tin oxide, zirconium oxide, and aluminum oxide. Zinc oxide particles tend to increase the transmittance of the undercoat layer and are thus effective in producing the advantageous effect of the embodiment.

Examples of the solvent used in the coating liquid for the undercoat layer include alcohol-based compounds, sulfoxide-based compounds, ketone-based compounds, ether-based compounds, ester-based compounds, halogenated aliphatic hydrocarbon compounds, aromatic compounds, and other organic compounds.

The undercoat layer may further contain an organic resin fine particles and a levelling agent.

The transmittance of the undercoat layer for light having a wavelength in the visible region varies depending mainly on the particle size and content of the metal oxide particles, the particle size and content of the organic resin fine particles and the thickness of the undercoat layer. Therefore, the transmittance can be controlled by varying these factors.

For example, the metal oxide particles preferably have an average particle size of 1 μm or less, more preferably in the range of 0.01 μm to 0.5 μm. The ratio of the metal oxide particle content to the binding resin content in the undercoat layer is preferably 2:1 to 4:1 (on a mass basis).

The average particle size of the organic resin fine particles is preferably in the range of 0.5 μm to 5 μm. The organic resin fine particle content in the undercoat layer is preferably 20% by mass or less relative to the total solid content of the undercoat layer.

The thickness of the undercoat layer is preferably in the range of 0.5 μm to 30 μm, more preferably in the range of 1 μm to 25 μm.

Photosensitive Layer (Charge Generation Layer)

A charge generation layer is disposed on the undercoat layer. The charge generation material of the charge generation layer absorbs light used in the testing step. More specifically, examples of the charge generation material include azo pigments, phthalocyanine pigments, indigo pigments, perylene pigments, polycyclic quinone pigments, squarylium dyes, thiapyrylium salts, triphenylmethane dyes, quinacridone pigments, azulenium salt pigments, cyanine dyes, anthanthrone pigments, pyranthrone pigments, xanthene dyes, quinonimine dyes, and styryl dyes. These charge generation materials may be used singly or in combination. Among these materials, phthalocyanine pigments and azo pigments, particularly phthalocyanine pigments, may be suitably used from the viewpoint of enhancing the photosensitivity of the charge generation layer.

Among phthalocyanine pigments, oxytitanium phthalocyanine, chlorogallium phthalocyanine, and hydroxygallium phthalocyanine are advantageous in charge generation efficiency. From the viewpoint of photosensitivity, crystalline hydroxygallium phthalocyanine is particularly advantageous whose CuKα X-ray diffraction spectrum shows peaks at Bragg angle 2θ of 7.4°±0.3° and 28.2°±0.3°.

Examples of the binding resin used in the charge generation layer include acrylic resin, allyl resin, alkyd resin, epoxy resin, diallylphthalate resin, styrene-butadiene copolymer, butyral resin, benzar resin, polyacrylate resin, polyacetal resin, polyamide-imide resin, polyamide resin, polyallyl ether resin, polyacrylate resin, polyimide resin, polyurethane resin, polyester resin, polyethylene resin, polycarbonate resin, polystyrene resin, polysulfone resin, polyvinyl acetal resin, polybutadiene resin, polypropylene resin, methacrylic resin, urea resin, vinyl chloride-vinyl acetate copolymer, vinyl acetate resin, and vinyl chloride resin. Among these, butyral resin may be suitably used. These binding resins may be used singly, or may be combined to be used as a mixture or a copolymer.

The charge generation layer can be formed by applying a charge generation coating liquid prepared by dispersing a charge generation material and a binding resin in a solvent to form a coating film and drying the coating film. Alternatively, the charge generation layer may be a deposition layer formed by depositing a charge generation material.

The dispersion is performed using, for example, a homogenizer, an ultrasonic disperser, a ball mill, a sand mill, a roll mill, a vibration mill, an attritor, or a high-speed liquid collision disperser.

The proportion of the charge generation material is preferably in the range of 0.3 parts by mass to 10 parts by mass relative to 1 part by mass of the binding resin.

Examples of the solvent used in the charge generation coating liquid include alcohol-based compounds, sulfoxide-based compounds, ketone-based compounds, ether-based compounds, ester-based compounds, halogenated aliphatic hydrocarbon compounds, and aromatic compounds. The thickness of the charge generation layer is preferably in the range of 0.01 µm to 5 µm, more preferably in the range of 0.1 µm to 2 µm. The charge generation layer may further contain additives, such as a sensitizer, an antioxidant, a UV absorbent, and a plasticizer.

Photosensitive Layer (Charge Transport Layer)

A charge transport layer is disposed on the charge generation layer. Examples of the charge transport material used in the charge transport layer include triarylamine compounds, hydrazone compounds, styryl compounds, stilbene compounds, and butadiene compounds. These charge transport materials may be used singly or in combination. From the viewpoint of charge mobility, triarylamine compounds may be suitably used.

If the photosensitive layer has a multilayer structure, examples of the binding resin used in the charge transport layer include acrylic resin, acrylonitrile resin, allyl resin, alkyd resin, epoxy resin, silicone resin, phenol resin, phenoxy resin, polyacrylamide resin, polyamide-imide resin, polyamide resin, polyallyl ether resin, polyacrylate resin, polyimide resin, polyurethane resin, polyester resin, polyethylene resin, polycarbonate resin, polysulfone resin, polyphenylene oxide resin, polybutadiene resin, polypropylene resin, and methacrylic resin. Among these, polyacrylate resin and polycarbonate resin may be suitably used. These binding resins may be used singly, or may be combined to be used as a mixture or a copolymer.

The charge transport layer can be formed by applying a charge transport coating liquid prepared by dispersing a charge transport material and a binding resin in a solvent to form a coating film and drying the coating film. The proportion of the charge transport material in the charge transport layer is preferably in the range of 0.3 parts by mass to 10 parts by mass relative to 1 part by mass of the binding resin. From the viewpoint of suppressing cracks in the charge transport layer, the coating film of the charge transport coating liquid is dried preferably at a temperature in the range of 60° C. to 150° C., more preferably in the range of 80° C. to 120° C. The drying time is preferably in the range of 10 minutes to 60 minutes.

Examples of the solvent used in the charge transport coating liquid include alcohol-based compounds, such as propanol and butanol (particularly alcohols having a carbon number of 3 or more); aromatic hydrocarbon-based compounds, such as anisole, toluene, xylene, and chlorobenzene; and methyl cyclohexane and ethyl cyclohexane.

If the charge transport layer of the electrophotographic photoreceptor is composed of a single layer, the thickness of the charge transport layer is preferably in the range of 5 µm to 40 µm, more preferably in the range of 8 µm to 30 µm. If the charge transport layer has a multilayer structure, the thickness of the charge transport layer close to the support member is preferably in the range of 5 µm to 30 µm, and the thickness of the charge transport layer close to the surface is preferably in the range of 1 µm to 10 µm.

The charge transport layer may further contain an antioxidant, a UV absorbent, a plasticizer, or any other additive.

In an embodiment of the present invention, in order to protect the photosensitive layer and enhance the abrasion resistance and cleanability of the photosensitive layer, a protective layer (second charge transport layer) may be provided over the photosensitive layers.

The protective layer can be formed by applying a coating liquid of the protective layer prepared by dissolving a binding resin in an organic solvent to form a coating film and drying the coating film. Examples of the resin used in the protective layer include polyvinyl butyral resin, polyester resin, polycarbonate resin, polyamide resin, polyimide resin, polyacrylate resin, polyurethane resin, styrene-butadiene copolymer, styrene-acrylic acid copolymer, and styrene-acrylonitrile copolymer.

In order to enable the protective layer to transport charges, the protective layer may be formed by curing a monomer capable of transporting charges or a polymeric charge transport material by a crosslinking reaction. For example, a charge-transportable compound having a chain-polymerizable functional group may be polymerized or crosslinked to be cured. Exemplary chain-polymerizable functional groups include acrylic, methacrylic, alkoxysilyl, and epoxy. Examples of reactions for curing the charge-transportable compound include radical polymerization, ionic polymerization, thermal polymerization, photopolymerization, radiation-induced polymerization (electron beam polymerization), plasma CVD, and optical CVD.

The thickness of the protective layer is preferably in the range of 0.5 µm to 10 µm, more preferably in the range of 1 µm to 7 µm. Furthermore, electrically conductive particles or the like may be added to the protective layer.

To the uppermost layer (charge transport layer or protective layer) of the electrophotographic photoreceptor, other additives may be added, such as silicone oil, wax, polytetrafluoroethylene particles or any other fluorine-containing organic resin particles, silica particles, alumina particles, and boron nitride or any other lubricant.

The coating liquids of the respective layers can be applied by immersion coating, spray coating, spinner coating, roller coating, mayer bar coating, blade coating, or any other coating technique.

Large-Scale Manufacturing Process of Electrophotographic Photoreceptor

The above-described method for testing the charge generation layer may be applied to a process for manufacturing electrophotographic photoreceptors on a large scale.

More specifically, in the process according to an embodiment of the present invention, a plurality of electrophotographic photoreceptors are manufactured on a large scale. This process includes the first step of preparing objects to be tested, each including an aluminum-based cylindrical support member formed by extrusion and drawing having a periphery not subjected to cutting work, an undercoat layer formed directly on the periphery of the support member, and a charge generation layer disposed directly on the undercoat layer. After the first step, the second step is performed of testing each charge generation layer for a defect or a suspected defect by irradiating the charge generation layer of the object with light, and receiving light reflected from the charge generation layer with a light-receiving device, thus grouping the objects into the following three groups:

(a) objects having a defect in the charge generation layer;

(b) objects having a suspected defect in the charge generation layer; and (c) objects having no defect or suspected defect in the charge generation layer.

Then, after the second step, the third step is performed of heat-treating the objects applicable to either:

(i) objects grouped into (b), but judged in a subsequent visual observation that the suspected defect is not a defect in the charge generation layer; or (ii) objects grouped into (c).

The undercoat layer has a transmittance of 1% or more for light having a wavelength in the visible region, and the light with which the charge generation layer is irradiated in the second step has a wavelength within the range of the absorption wavelengths of the charge generation layer, and whose transmittance to the undercoat layer is 0.3% or less.

In the second step, unevenness in the thickness of the charge generation layer is separated from unevenness of the aluminum-based support member formed by extrusion and drawing whose periphery is not subjected to cutting work. Thus, it can be avoided that the charge generation layer is judged to be defective even though the charge generation layer has an even thickness. This increases the efficiency in large-scale manufacture.

EXAMPLES

The present invention will be further described in detail with reference to specific examples. However, the present invention is not limited to the examples disclosed below. The term "part(s)" used hereinafter refers to "part(s) by mass".

Production Example 1

Support Member

Twenty aluminum-based cylinders of 30 mm in diameter and 357.5 mm in length were formed as support members (electrically conductive members) by extrusion and drawing. The peripheries of the cylinders were not subjected to cutting work.

—Undercoat Layer

Subsequently, 100 parts of zinc oxide particles (specific surface area: 19 m$^2$/g, powder resistance: 4.7×10$^6$ Ω·cm) was mixed with 500 parts of toluene, followed by stirring. Then, 0.8 part of a silane coupling agent (N-2-(aminoethyl)-3-aminopropylmethyldimethoxy silane, KBM 602 (trade name), produced by Shin-Etsu Chemical) was added to the mixture, followed by stirring for 6 hours. After the toluene was removed by evaporation under reduced pressure, the sample was dried by heating at 130° C. for 6 hours to yield surface-treated zinc oxide particles.

Subsequently, 15 parts of a butyral resin BM-1 (produced by Sekisui Chemical Co., Ltd) and 15 parts of a blocked isocyanate Sumidur 3175 (produced by Sumitomo Bayer Urethane Company Ltd.) were dissolved in a mixed solution of 73.5 parts of methyl ethyl ketone and 73.5 parts of 1-butanol. To the resulting solution were added 80.64 parts of the surface-treated zinc oxide particles and 0.4 part of 2,3,4-trihydroxybenzophenone (produced by Wako Pure Chemical Industries, Ltd.). These materials were dispersed into each other in a sand mill with glass beads of 0.8 mm in diameter at 23° C.±3° C. for 3 hours.

To the dispersion were added 0.01 part of silicone oil SH28PA produced by Dow Corning Toray Silicone Co., Ltd.) and 5.6 parts of crosslinked poly(methyl methacrylate) (PMMA) particles TECHPOLYMER SSX-103 (produced by Sekisuki Chemical Co., Ltd., average primary particle size: 3.0 μm) to yield an undercoating liquid.

The undercoating liquid was applied onto the support member by immersion coating, and the resulting coating film was dried at 160° C. for 40 minutes, thus forming a 18 μm thick undercoat layer.

—Charge Generation Layer

Subsequently, crystalline hydroxygallium phthalocyanine (charge generation material) whose CuKα X-ray diffraction spectrum has peaks at Bragg angle 2θ of 7.4°±0.2° and 28.1°±0.2° were prepared. To a solution of 2 parts of a polyvinyl butyral resin S-LEC BX-1 (produced by Sekisui Chemical Co., Ltd.) in 100 parts of cyclohexanone, 4 parts of the crystalline hydroxygallium phthalocyanine and 0.04 part of a compound expressed by the following formula (A) were added.

Then, the materials were dispersed into each other in a sand mill with glass beads of 1 mm in diameter at 23° C.±3° C. for 1 hour. To the resulting dispersion was added 100 parts of ethyl acetate to yield a charge generation coating liquid. The charge generation coating liquid was applied onto the undercoat layer by immersion coating. The resulting coating film was dried at 90° C. for 10 minutes to yield a 0.21 μm thick charge generation layer.

Samples including a charge generation layer having an uneven thickness and samples including a charge generation layer having an even thickness For testing for unevenness in thickness, 10 samples each including a charge generation layer having an uneven thickness and 11 samples each including a charge generation layer having an even thickness were prepared. The charge generation layer having an uneven thickness was formed by drying the coating film at 90° C. for 10 minutes, immediately after immersion coating, while part of the coating film was blown.

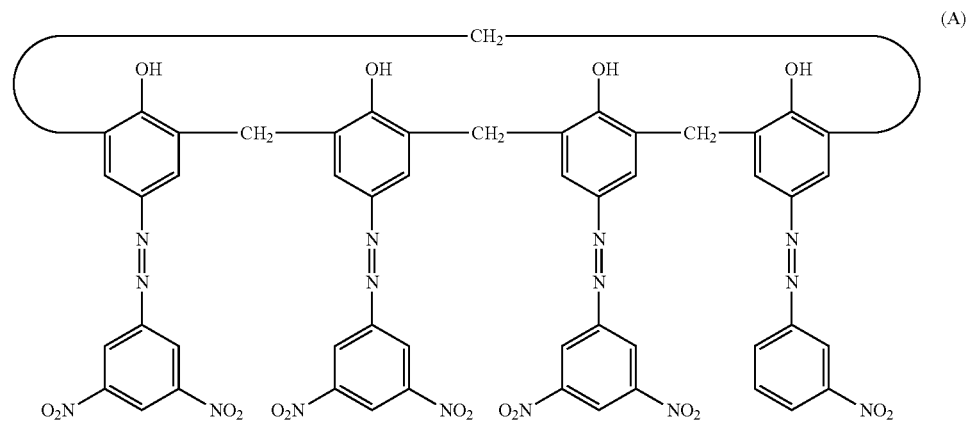

(A)

—Charge Transport Layer (First Charge Transport Layer)

Subsequently, a charge transport coating liquid was prepared by dissolving 50 parts of the compound (charge transport material) expressed by the following formula (B), 50 parts of the compound (charge transport material) expressed by the following formula (C), and 100 parts of a polycarbonate resin IUPILON Z400 (produced by Mitsubishi Gas Chemical Company, Inc.) in a mixed solvent of 650 parts of chlorobenzene and 150 parts of dimethoxymethane.

The charge transport coating liquid uniformly blended was allowed to stand for one day, and then applied onto the charge generation layer. The resulting coating film was dried at 110° C. for 60 minutes to yield a 18 μm thick charge transport layer (first charge transport layer).

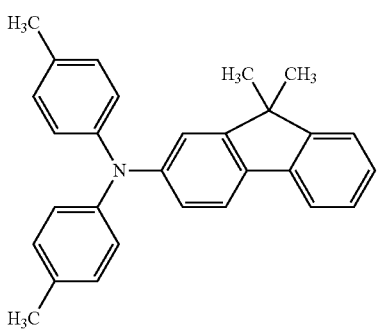

—Protective Layer (Second Charge Transport Layer)

Subsequently, a protective coating liquid was prepared by mixing and dispersing 36 parts of a compound (charge transport material having a chain-polymerizable functional group acryloyloxy) expressed by the following formula (D), 4 parts of polytetrafluoroethylene resin particles (LUBRON L-2, produced by Daikin Industries, Ltd.), and 60 parts of n-propanol in a super high-pressure disperser.

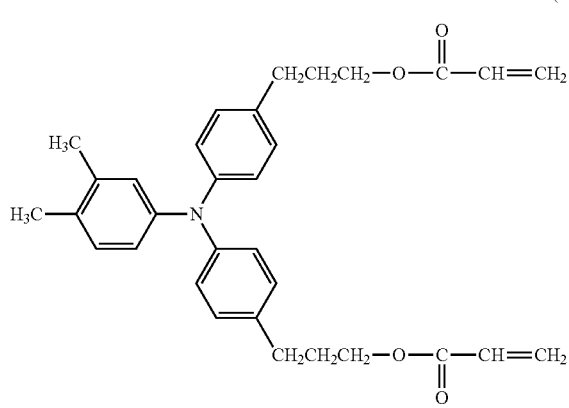

The protective coating liquid was applied onto the charge transport layer by immersion coating, and the coating film was dried at 50° C. for 5 minutes. After being dried, the coating film was cured by being irradiated with an electron beam at an acceleration voltage of 70 kV and an absorbed dose of 8000 Gy for 1.6 s in a nitrogen atmosphere while the cylinder was being rotated. Then, the cured coating film was heat-treated in a nitrogen atmosphere for 3 minutes under the condition where the coating film temperature came to 120° C. The oxygen concentration was 20 ppm in the operations from the electron beam irradiation to the 3-minute heat treatment. Subsequently, the coating film was heat-treated for 30 minutes in the air under the condition where the coating film temperature came to 100° C., thus yielding a 5 μm thick protective layer (second charge transport layer).

Thus, electrophotographic photoreceptor samples, each including a support member, an undercoat layer, a charge generation layer, a charge transport layer (first charge transport layer) and a protective layer (second charge transport layer) in that order, were prepared for testing the charge generation layer for unevenness in thickness.

Each of the electrophotographic photoreceptor samples was mounted in a copy machine imageRUNNER iR-ADV C5051 manufactured by Canon, and half-tone images were formed.

Half-tone images formed using the samples including a charge generation layer having an even thickness did not exhibit unevenness. More specifically, streaks resulting from the aluminum-based cylindrical support member formed by extrusion and drawing and having a periphery not subjected to cutting work did not appear in the images. On the other hand, half-tone images formed using the samples including a charge generation layer having an uneven thickness exhibited unevenness.

Thus, in the step of testing the charge generation layer for unevenness in thickness, the charge generation layer having an even thickness should be judged to be not defective, and the charge generation layer having an uneven thickness should be judged to be defective.

Production Example 2

Samples for testing the charge generation layer for unevenness in thickness were prepared by forming members or layers up to the charge transport layer in the same manner as in Production Example 1, without forming the protective layer (second charge transport layer).

Production Example 3

Samples for testing the charge generation layer for unevenness in thickness were prepared by forming members or layers up to the charge generation layer in the same manner as in Production Example 1, without forming the charge transport layer (first charge transport layer) or the protective layer (second charge transport layer).

Production Example 4

Twenty aluminum-based cylinders of 30 mm in diameter and 357.5 mm in length were formed as support members (electrically conductive members) by extrusion and drawing. The peripheries of the cylinders were not subjected to cutting work.

Subsequently, 100 parts of zinc oxide particles (specific surface area: 19 $m^2$/g, powder resistance: $4.7 \times 10^6$ Ω·cm) was mixed with 500 parts of toluene, followed by stirring. Then, 0.8 part of a silane coupling agent (N-2-(aminoethyl)-3-aminopropylmethyldimethoxy silane, KBM 602 (trade name), produced by Shin-Etsu Chemical) was added to the mixture, followed by stirring for 6 hours.

After the toluene was removed by evaporation under reduced pressure, the sample was dried by heating at 130° C. for 6 hours to yield surface-treated zinc oxide particles.

Subsequently, 15 parts of a butyral resin BM-1 (produced by Sekisui Chemical Co., Ltd) and 15 parts of a blocked isocyanate Sumidur 3175 (produced by Sumitomo Bayer Urethane Company Ltd.) were dissolved in a mixed solution of 73.5 parts of methyl ethyl ketone and 73.5 parts of 1-butanol.

To the resulting solution were added 80.64 parts of the surface-treated zinc oxide particles, 0.4 part of 2,3,4-trihydroxybenzophenone (produced by Wako Pure Chemical Industries, Ltd.), and 10 parts of zinc oxide particles LPZ-INC-2 (produced by Sakai Chemical Industry Co., Ltd.). These materials were dispersed into each other in a sand mill with glass beads of 0.8 mm in diameter at 23° C.±3° C. for 3 hours. To the resulting dispersion was added 0.01 part of silicone oil (SH28PA, trade name) to yield an undercoating liquid.

The undercoating liquid was applied onto the support member by immersion coating, and the resulting coating film was dried at 160° C. for 40 minutes, thus forming a 18 µm thick undercoat layer.

Subsequently, a charge generation layer and a charge transport layer were formed in the same manner as in Production Example 1. Thus, samples for testing the charge generation layer for unevenness in thickness were completed.

Example 1

The samples prepared in Production Example 1 were subjected to evaluation as described later. The light source used in the testing step was a high-luminance LED straight light (manufactured by Aitech System Co., Ltd., blue LED, central wavelength: 450 nm). The evaluation results are shown in the Table.

Example 2

Samples were subjected to evaluation in the same manner as in Example 1, except for the following. The samples prepared in Production Example 2 were used. After testing the charge generation layer for unevenness in thickness, the support member was heat-treated at 100° C. for 60 minutes.

Example 3

Samples were subjected to evaluation in the same manner as in Example 1, except for the following. The samples prepared in Production Example 3 were used. After testing the charge generation layer for unevenness in thickness, the support member was heat-treated at 100° C. for 60 minutes.

Example 4

Samples were subjected to evaluation in the same manner as in Example 1, except for the following. The samples prepared in Production Example 2 were used. After testing the charge generation layer for unevenness in thickness, the protective layer (second charge transport layer) was not formed.

Example 5

Samples were subjected to evaluation in the same manner as in Example 1, except for the following. After testing the charge generation layer for unevenness in thickness, the support member was heat-treated at 100° C. for 60 minutes.

Example 6

Samples were subjected to evaluation in the same manner as in Example 2, except for the following. The samples prepared in Production Example 4 were used.

Comparative Example 1

Samples were evaluated in the same manner as in Example 1, except that a green LED having a central wavelength of 525 nm was used as the light source.

Comparative Example 2

Samples were evaluated in the same manner as in Example 1, except that a red LED having a central wavelength of 630 nm was used as the light source.

Comparative Example 3

Samples were evaluated in the same manner as in Example 6, except that a red LED having a central wavelength of 630 nm was used as the light source.

Evaluation

Evaluation for Examples 1 to 6 and Comparative Examples 1 to 3 was performed as below.

Measurement of Absorbance

In order to confirm that the wavelength of the light used in the testing step of Examples and Comparative Examples was within the range of the absorption wavelengths of the charge generation layer, absorbance was measured.

An ultraviolet-visible spectrophotometer V-570 (manufactured by JASCO Corporation) was used for measuring absorbance. The charge generation coating liquid prepared in Production Example 1 was applied onto a glass plate by immersion coating under the same conditions, and dried to yield the same charge generation layer having the same thickness as in Production Example 1.

The absorbance of the charge generation layer was measured in a fixed wavelength measurement mode of the spectrophotometer. First, only a glass plate was placed at the measuring position and the reading of absorbance of the spectrophotometer was adjusted to zero for zero pint adjustment.

Subsequently, the glass plate on which the charge generation layer had been formed was placed at the measuring position. The absorbances of the charge generation layer were measured at wavelengths of 450 nm, 525 nm and 630 nm. The measured absorbances of the charge generation layer were 0.11, 0.10 and 0.72 at the respective wavelengths. It was thus confirmed that the wavelengths of the light used in the testing step were within the range of the absorption wavelengths of the charge generation layer.

Measurement of Transmittance

The transmittances of the undercoat layers of Production Examples 1 and 4 were measured. An ultraviolet-visible spectrophotometer V-570 (manufactured by JASCO Corporation) was used for measuring transmittance. The undercoating liquids prepared in Production Examples 1 and 4 were applied onto respective glass plates by immersion coating under the same conditions, and dried to yield the same charge generation layers having the same thicknesses as in Production Examples 1 and 4, respectively.

The transmittance was measured in a fixed wavelength measurement mode of the spectrophotometer. First, only a glass plate was placed at the measuring position and the reading of transmittance of the spectrophotometer was adjusted to 100% for zero pint adjustment.

Subsequently, the glass plate on which the undercoat layer had been formed was placed at the measuring position. The transmittance of the undercoat layer was measured at 780 nm. The transmittances of the undercoat layers of Production Examples 1 and 4 were 2.5% and 1.2%, respectively. It was confirmed that the transmittances of both undercoat layers were 1% or more for light having a wavelength in the visible region.

Furthermore, the transmittances of the undercoat layers of the Production Examples 1 and 4 were measured for light having the same wavelength as the light emitted from the light source used in the testing step. The results are shown in the Table.

A copy machine imageRUNNER iR-ADV C5051 manufactured by canon Inc., modified so that potential could be measured was used as the electrophotographic apparatus for evaluation.

The electrophotographic photoreceptor and the electrophotographic apparatus were allowed to stand under room temperature and normal humidity (23° C., 50% RH) for one hour. First, an untested electrophotographic photoreceptor was mounted to the electrophotographic apparatus, and the amount of laser light was adjusted to a bright potential of −150 V. Subsequently, a tested electrophotographic photoreceptor was mounted. The bright potential was measured, and the difference ($\Delta VL$) in bright potential between the untested electrophotographic photoreceptor and the tested electrophotographic photoreceptor was calculated. The results are shown in the Table.

TABLE

| | Production Example | Wavelength used for test | Undercoat layer transmittance | Test of charge generation layer having uneven thickness | | Test of charge generation layer having even thickness | | Heat treatment after test | $\Delta VL$ |
| | | | | Number of samples judged to be defective | Number of samples judged to be not defective | Number of samples judged to be defective | Number of samples judged to be not defective | | |
| --- | --- | --- | --- | --- | --- | --- | --- | --- | --- |
| Example 1 | 1 | 450 nm | 0.3% | 10 | 0 | 0 | 10 | Not applied | 5 V |
| Example 2 | 2 | 450 nm | 0.3% | 10 | 0 | 0 | 10 | Applied | 0 V |
| Example 3 | 3 | 450 nm | 0.3% | 10 | 0 | 0 | 10 | Applied | 0 V |
| Example 4 | 2 | 450 nm | 0.3% | 10 | 0 | 0 | 10 | Not Applied | 4 V |
| Example 5 | 1 | 450 nm | 0.3% | 10 | 0 | 0 | 10 | Applied | 0 V |
| Example 6 | 4 | 450 nm | 0.2% | 10 | 0 | 0 | 10 | Applied | 0 V |
| Comparative Example 1 | 1 | 525 nm | 0.6% | 10 | 0 | 8 | 2 | Not Applied | 1 V |
| Comparative Example 2 | 1 | 630 nm | 1.2% | 10 | 0 | 10 | 0 | Not Applied | 0 V |
| Comparative Example 3 | 4 | 630 nm | 0.5% | 10 | 0 | 8 | 2 | Applied | 0 V |

Test of Charge Generation Layer for Unevenness in Thickness

The samples including a charge generation layer having an uneven thickness (samples intentionally formed so as to have an uneven thickness) and the samples including a charge generation layer having even thickness, prepared in the Production Examples, were tested using the light source and light-receiving device shown in FIG. 1. The wavelengths of the light source used in the Examples and Comparative Examples are shown in the Table. Ten samples having uneven thicknesses and ten samples having even thicknesses were tested, and the number of the samples judged to be defective or to be not defective was evaluated from the difference in the intensity of reflected light. The results are shown in the Table.

Evaluation of Photo Memory

For evaluation, samples having even thicknesses tested in Examples 1 to 6 and Comparative Examples 1 to 3 and untested samples having even thickness were used. For the tested samples not having a protective layer (second charge transport layer), protective layers were formed after the testing step by coating and drying in the same manner as in Production Example 1, and thus electrophotographic photoreceptors were prepared.

In the Table, "test of charge generation layer having uneven thickness" refers to the test of charge generation layers having uneven thicknesses for unevenness in thickness. Also, "test of charge generation layer having even thickness" refers to the test of charge generation layers having even thicknesses for unevenness in thickness.

In Examples 1 to 6, the samples including a charge generation layer having an uneven thickness were all judged to be defective, while the samples including a charge generation layer having an even thickness were all judged to be not defective, as shown in the Table.

On the other hand, in Comparative Examples 1 and 3, some of the samples including a charge generation layer having an even thickness were judged to be defective. In Comparative Example 2, the samples including a charge generation layer having an even thickness were all judged to be defective.

The reason why some or all of the samples including a charge generation layer having an even thickness were judged to be defective in Comparative Examples 1 to 3 is that the light used for the test was transmitted to the surface of the support member through the undercoat layer. Consequently, the intensity of the light reflected from the surface of the support member was varied according to the unevenness of the surface of the support member.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-076503 filed Apr. 1, 2013, which is hereby incorporated by reference herein in its entirety.

What is claimed is:

1. A method for inspecting a charge generation layer of an object including an aluminum-based cylindrical support member formed by extrusion and drawing having a periphery free of cutting work, an undercoat layer disposed directly on the periphery of the support member and having a transmittance of 1% or more for light having a wavelength in the visible region, and the charge generation layer disposed directly on the undercoat layer and having absorption wavelengths, the method comprising:
    testing the charge generation layer for a defect or a suspected defect by:
        irradiating the charge generation layer with light, and
        receiving reflected light from the charge generation layer with a light receiving device,
    wherein the light has a wavelength within the range of the absorption wavelengths of the charge generation layer, and transmittance to the undercoat layer of the light is 0.3% or less.

2. The method according to claim 1, wherein the object further includes a charge transport layer disposed directly on the charge generation layer.

3. The method according to claim 1, wherein the testing of the charge generation layer is judged according to difference in the intensity of the reflected light.

4. The method according to claim 1, wherein the charge generation layer comprises a phthalocyanine pigment.

5. The method according to claim 1, wherein the undercoat layer comprises zinc oxide particles.

6. A method for manufacturing a plurality of electrophotographic photoreceptors on a large scale, the method comprising:
    producing objects to be tested, the objects each including an aluminum-based cylindrical support member formed by extrusion and drawing having a periphery free of cutting work, an undercoat layer disposed directly on the periphery of the support member and having a transmittance of 1% or more for light having a wavelength in the visible region, and a charge generation layer disposed directly on the undercoat layer and having absorption wavelengths;
    testing each charge generation layer for a defect or a suspected defect by irradiating the charge generation layer with light, receiving reflected light from the charge generation layer with a light-receiving device, and grouping the objects into the following three groups:
    (a) objects having a defect in the charge generation layer;
    (b) objects having a suspected defect in the charge generation layer; and
    (c) objects having no defect or suspected defect in the charge generation layer; and
    heat-treating the objects applicable to either:
    (i) objects of group (b), but judged in a visual test that the suspected defect is not a defect in the charge generation layer; or
    (ii) objects grouped into (c),
    wherein the light has a wavelength within the range of the absorption wavelengths of the charge generation layer and transmittance to the undercoat layer of the light is 0.3% or less.

7. The method according to claim 6, wherein the object further includes a charge transport layer disposed directly on the charge generation layer.

8. The method according to claim 6, wherein the testing of the charge generation layer is judged according to difference in the intensity of the reflected light.

9. The method according to claim 6, wherein the charge generation layer comprises a phthalocyanine pigment.

10. The method according to claim 6, wherein the undercoat layer comprises zinc oxide particles.

* * * * *